United States Patent [19]

Crounse et al.

[11] 4,320,140
[45] Mar. 16, 1982

[54] SYNERGISTIC INSECTICIDAL COMPOSITIONS

[75] Inventors: Nathan N. Crounse, Myrtle Beach, S.C.; James R. Heitz, Starkville, Miss.

[73] Assignee: Sterling Drug Inc., New York, N.Y.

[21] Appl. No.: 195,527

[22] Filed: Oct. 9, 1980

[51] Int. Cl.³ ............................................ A01N 43/16
[52] U.S. Cl. .................................................... 424/283
[58] Field of Search ......................................... 424/283

[56] References Cited
PUBLICATIONS

A. Barbieri, "Revista di Malariologica", 7:456–463 (1928) & translation.
H. Schildmacher, "Biol. Zentr.", 69:468–477 (1950) & translation.
J. E. Fondren, Jr. et al., "Environmental Entomology", 7, No. 6, 843–846 (1978).
J. R. Broome et al., "Environmental Entomology", 4, No. 6:883–886.
Yoho et al., "J. Economic Entomology", 64 972–973 (1971).
Heitz et al., "Disposal and Decontamination of Pesticides", ACS Symposium Series, No. 73 (1978).

*Primary Examiner*—Frederick E. Waddell
*Attorney, Agent, or Firm*—Lynn T. Fletcher; B. Woodrow Wyatt

[57] ABSTRACT

Synergistic insecticidal compositions are mixtures of at least one insecticidally active water-soluble xanthene dye chosen from amongst erythrosine and Rose Bengal in admixture with the essentially non-insecticidally active and synergistically-effective fluorescein sodium.

9 Claims, No Drawings

SYNERGISTIC INSECTICIDAL COMPOSITIONS

BACKGROUND OF THE INVENTION

1. Field of the Invention

The present invention relates to novel synergistic insecticidal compositions which are mixtures of water-soluble xanthene dyes, and which comprise at least one insecticidally active dye chosen from amongst erythrosine and Rose Bengal in admixture with the essentially non-insecticidally active fluorescein sodium, and to a method of combating insects with said mixtures.

2. Description of the Prior Art

Both erythrosine and Rose Bengal employed individually, as well as in admixture with each other, are known to be effective as insecticides. In the most relevant prior art, the insecticidal activity is generally attributed to a photodynamic action of visible light on insects or their larvae pretreated with the dyes in the dark followed by exposure to visible light.

A. Barbieri, Rivista di Malariologica 7:456–63 (1928) discloses that when 15 mosquito (Culex) larvae were treated with an aqueous solution of Rose Bengal at a concentration of 1:30,000 and held in the dark for several hours, all the larvae died within three hours on being exposed to diffuse solar light. Barbieri also reported that "several larvae and pupae", when treated with an aqueous solution containing a mixture of erythrosine and Rose Bengal at a concentration of 1:30,000 and held in the dark for several hours, died (except for 1 pupae) within two and a half hours on being exposed to diffuse (solar) light.

H. Schildmacher, Biol. Zentr. 69:468–77 (1950) discloses that Rose Bengal and erythrosine, each used independently at a concentration of 1:100,000, have larvicidal activity against second and third instar larvae of the mosquito (Anopheles maculipennis) upon immediate exposure of the treated larvae to direct sunlight for 130 minutes, but that Uranin (fluorescein sodium) was rejected as a potential insecticide because, under the same test conditions, 32 out of 40 larvae survived as compared to 39 out of 40 surviving among the untreated control larvae. In the case of erythrosine, 5 out of 40 larvae survived, and in the case of Rose Bengal, none of the 40 larvae survived. This author also reports that survival prior to exposure to light of larvae pretreated in the dark with erythrosine and Rose Bengal was equal to or better than survival of larvae held only in water in the dark for the same period of time.

J. E. Fondren, Jr. and J. R. Heitz, Environmental Entomology 7, no. 6:843-6 (1978) disclose that erythrosine and Rose Bengal singly fed to adult face flies (Musca autumnalis), each at a concentration of $5 \times 10^3$ M in a 2 percent milk sugar solution, and the flies held in the dark followed by exposure to fluorescent light, produces $LT_{50}$ values of 8.16 hours and 1.53 hours, respectively while the same concentration of fluorescein sodium produces a $LT_{50}$ value greater than 48 hours.

J. R. Broome, M. F. Callaham and J. R. Heitz, Environmental Entomology 4, no. 6:883–886 (1975) disclose that both erythrosine and Rose Bengal are photodynamically lethal to the black imported fire ant (Solenopis richteri) when separately fed to the test insect in the dark for 24 hours in a concentration of $5 \times 10^{-3}$ M in a 1 percent sucrose solution followed by exposure to fluorescent light for varying periods of time.

T. P. Yoho, J. E. Weaver, and L. Butler, J. Economic Entomology 64:972–3 (1971) disclose that house flies (Musca domestica) prefed (in the dark) either erythrosine or Rose Bengal dissolved in milk sugar solution at a concentration of 0.125 percent have a mortality after exposure to natural light of 89 and 100 percent, respectively, while fluorescein sodium fed under the same conditions and concentrations exhibits no mortality.

J. R. Heitz and W. W. Wilson in Disposal and Decontamination of Pesticides, ACS Symposium Series, No. 73 (1978) disclose that the xanthene dyes erythrosine, Rose Bengal and fluorescein sodium have half-lives in visible light on the order of hours and that the photodegraded residual material is less toxic to insects (house flies) and bacteria than the undegraded dyes.

SUMMARY OF THE INVENTION

The present invention provides synergistic insecticidal compositions, which are mixtures of water-soluble xanthene dyes, and which contain as the active ingredient at least one insecticidally active dye chosen from amongst erythrosine and Rose Bengal, and as the synergism effecting ingredient, the essentially non-insecticidal fluorescein sodium, also known as uranine.

This invention also provides for a method of combating or killing insects which comprises contacting the insects or their larvae with insecticidally effective amounts of the synergistic insecticidal compositions of this invention.

DETAILED DESCRIPTION OF THE INVENTION INCLUSIVE OF THE PREFERRED EMBODIMENTS

More specifically, the invention sought to be patented resides in a synergistic insecticidal composition which is a mixture consisting essentially of an insecticidally effective amount of at least one insecticide chosen from the group consisting of erythrosine and Rose Bengal in combination with a synergistically effective amount of an alkali metal salt of fluorescein in the range of approximately 0.3 to 1.0 part by weight of the latter per part by weight of said insecticide.

In another of its aspects, the invention sought to be patented also resides in a method for combating or killing insects which comprises causing the insect to ingest a synergistic insecticidal composition which is a mixture consisting essentially of an insecticidally effective amount of at least one insecticide chosen from the group consisting of erythrosine and Rose Bengal in combination with a synergistically effective amount of an alkali metal salt of fluorescein in the range of approximately 0.3 to 1.0 part by weight of the latter per part by weight of said insecticide.

The terms "insecticide" and "insecticidal" are used herein to be inclusive of the lethal effect on both the larval and adult forms of the insect involved.

As used herein the term "synergistic insecticidal composition(s)" means a combination or mixture of at least one insecticidally active compound with an essentially non-insecticidally active compound wherein the insecticidal effectiveness of the mixture is greater than the sum of the effectiveness of each of the components of the combination.

As used herein, the term "mixture" as it refers to the combinations of fluorescein sodium, erythrosine B and Rose Bengal, is inclusive of mixtures of the solid forms of the dyes as well as aqueous solutions containing the dissolved dyes in admixture.

The water-soluble xanthene dyes used in preparing the synergistic compositions of this invention are all old and well known in the art, particularly the dyestuffs art. The insecticidal dye, erythrosine, is 2',4',5',7'-tetraiodofluorescein disodium salt and is also variously known as C.I. Acid Red 51, by Colour Index No. 45430, and erythrosine B. It has the structural formula

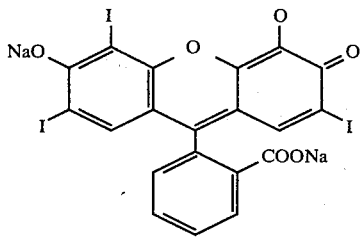

The insecticidal dye, Rose Bengal, is 4,5,6,7-tetrachloro-2',4,'5',7'-tetraidofluorescein dipotassium or disodium salt and is also variously known as C.I. Acid Red 94, Rose Bengale B and by Colour Index No. 45440. It is represented by the structural formula

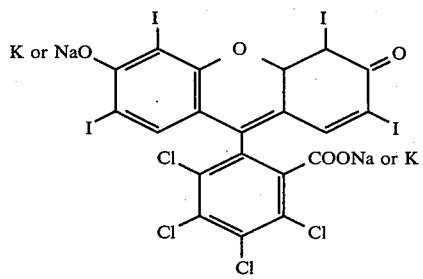

The essentially non-insecticidal dye fluorescein sodium is of the structural formula

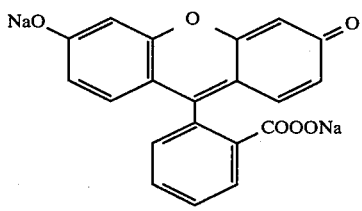

and is also variously known as uranine, C.I. Acid Yellow 73 and by Colour Index No. 45350.

In the present ecological climate, many highly effective insecticides, such as DDT and chlordane, have been banned or their use has been severely restricted because of their lasting toxicity to non-target animal life and the potential danger of residues spread to humans through water supplies and the food chain. Attempts have been made toward the development of effective insecticides which do not have this shortcoming. Amongst the compounds which have been found to be insecticidal without the undesired residue property are certain xanthene dyes. In particular, it has long been known that erythrosine and Rose Bengal possess a photodynamically-effected insecticidal activity on insects which have ingested the dyes. It is also known that these dyes, as well as the essentially non-insecticidal fluorescein sodium, which have utilities in the foodstuffs and pharmaceutical arts, are essentially non-toxic to mammals and have long been accepted as safe for human consumption or treatment. Moreover, it is also known that these dyes photodegrade in visible light in relatively short periods of time. Thus, erythrosine and Rose Bengal have desirable properties which make them acceptable for use as widely dispersible insecticides in the environment, for example, as mosquito and fly control agents.

Heretofore, the high cost of erythrosine and Rose Bengal has not made these compounds attractive as insecticides for widespread use. The present invention affords a means of overcoming this problem in that the synergistic effects obtained by combining the relatively inexpensive xanthene dye, fluorescein sodium with erythrosine and/or Rose Bengal substantially reduces the amount of the more expensive erythrosine and Rose Bengal needed to obtain an equivalent level of insecticidal activity. As a corollary to this, these insecticidal dyes can also be advantageously employed to obtain a faster rate of kill without using higher concentrations of said insecticidal dyes in those applications where more rapid insecticidal action is desired.

The best modes contemplated by the inventors of utilizing and carrying out this invention will now be described as to enable any person skilled in the art to which it pertains to make and use the same.

The synergistic insecticidal compositions of this invention can be prepared and utilized either in the form of intimately mixed finely-divided solids or in the form of aqueous solutions. The particular form is dependent upon the particular application that is desired. Thus, if a "bait" type application is desired, the bait can be impregnated with an aqueous solution form of the instant compositions. The solid form can also be used per se or can be blended with appropriate adjuvants as solid diluents or carriers, for example, sugar, talc, bentonite, kaolin or kieselguhr, for applications where broadcasting of the solid form is indicated or desired. Similarly, aqueous solutions of the instant composition optionally containing various adjuvants, such as surface-active agents, evaporation reducing agents and dispersing agents, can be used for widespread area distribution by spraying techniques.

Particularly useful for fly control are the "bait" type applications wherein the instant compositions are incorporated with sugar or sugar solutions. For example, any porous, absorbent inert material such as cotton, cellulose sponge, sphagnum moss and the like can be impregnated with a sugar solution prepared by dissolving the compositions of this invention therein and the impregnated material then formed into any of the generally-accepted forms for insecticidal bait applications.

The aqueous solutions of the instant synergistic insecticidal compositions are particularly useful for spraying applications. They are easily adapted for fly control in the dairy industry and the poultry industry where it is necessary to spray floors in dairy barns and the pits under caged layers in chicken houses. They are also useful in fly control in those animal breeding and rearing operations wherein the waste material produced by the animals presents a fly-control problem. Thus, the instant compositions can be utilized in aqueous sprays for treating the floors of holding pens in the beef and hog industries and pits beneath slot-floored pens. Both the solid forms and the solution forms of the subject compositions are useful for mosquito control. Thus, the water-soluble solid compositions can be dusted onto the surface of the water to be treated where it readily dissolves and becomes available for ingestion by the larvae. Alternatively, the solutions of the compositions can be sprayed on the surface of the water to be treated or can be dispersed therein by any art accepted methods.

When in solid form, the instant compositions are readily prepared by intimately mixing the measured-out components by any convenient means, for example, by ribbon blender, ball-mill or V-shell blender. The aqueous solution form of the compositions are readily prepared by simply sequentially or simultaneously dissolving the individual components in water at the desired concentration. Alternatively, stock solutions of known concentrations of each of the components can be prepared separately and measured volumes of the separate solutions can then be combined.

The ratios of the non-insecticidal alkali metal salt of fluorescein to the insecticidal erythrosine B and the Rose Bengal in the instant compositions can be rather broad and are limited only by the minimum and maximum amounts of said alkali metal salt of fluorescein which are synergistically effective. The ratios can thus be adjusted to fit the most attractive levels from the economic and insecticidal end results desired. A particularly preferred ratio range runs from approximately 0.3 to 1.0 part by weight of the alkali metal salt of fluorescein per part by weight of said insecticidal dye.

The concentration of the subject composition to be used in any insecticidal application, in either the solid form or in solution form, depends completely on such factors as the forms in which they are to be used, that is, bait, spray, dusting powder, and so forth, the nature and efficiency of diluent or carriers with which the compositions may be incorporated and the mode of use. Moreover, the compositions can be prepared in concentrated solution form to render them suitable for shipment and storage. The concentrates can then be diluted to the desired concentration for the intended application just prior to use.

The synergistic compositions of this invention are active against Diptera, particularly against the family Muscidae, for example, *Musca domestica* and the family Culicidae, for example, *Aedes triseriatus* and *Culex pipiens quinquefasciatus*.

The following examples serve to illustrate various insecticidal compositions of the invention and their efficacy against test larvae and insects. The testing protocol embodied in the examples generally parallels the art-recognized test protocol for insecticidal activity of xanthene dyes of pretreating the test insects in the dark followed by exposure to visible light. This testing protocol was employed in order to make equitable comparisons with the insecticidal dyes used singly in test procedures taught in the prior art. The examples are given for the purpose of illustration only, and not to limit the invention thereto.

EXAMPLE 1

A total of forty 250 ml capacity transparent plastic dishes were each charged with 100 ml of distilled water and ten fourth instar larvae of *Aedes triseriatus* (Diptera: Culicidae) were placed in each dish. A quantity of a $2.5 \times 10^{-3}$ M aqueous stock solution of Rose Bengal (w/v) sufficient to provide 102 ppm in final dilution was added to each dish in one set of ten dishes and a quantity of $2.5 \times 10^{-3}$ M aqueous stock solution of fluorescein sodium (w/v) sufficient to provide 61 ppm in final dilution was added to each dish in a second set of ten dishes. Like quantities of each of the stock solutions were then added to each dish in a third set of ten dishes to provide 102 ppm of Rose Bengal and 61 ppm of fluorescein sodium in combination in final dilution in each dish. The fourth set of ten dishes was held as a control with only the distilled water as the larval medium. An alfalfa tablet was added to each dish in all the sets as food and the insects were immediately incubated in total darkness for 18 hours prior to exposure to light. The incubation period allowed the larvae to ingest the dyes.

The larvae in the dishes were then uniformly exposed to light from paired Sylvania cool white fluorescent lamps which produced a photometer-measured intensity of the light at the surface of the solutions of 1250 $\mu E/m^2$.sec. Larval mortality was monitored hourly until approximately 50 percent mortality occurred in the larvae subjected to the Rose Bengal treatment. The criterion for death was lack of movement immediately after the larva was touched. Similarly, another set of four replications of each pre-treatment group (400 larvae per treatment) prepared as described above, were exposed to noon sunlight in Mississippi on a mid-July day. The intensity of the sunlight at the surface of the solutions fluctuated from 5600 to 6500 $\mu E/m^2$.sec as measured by a photometer because of atmospheric conditions. Larval mortality was monitored every ten minutes until approximately 50 percent mortality occurred in the larvae subjected to the Rose Bengal treatment. The results are summarized in the following table.

TABLE I

Percent Mortality of fourth instar *Aedes triseriatus* larvae upon treatment with the dye set fluorescein sodium/Rose Bengal and exposure to visible light

| Treatment | Dose (ppm) | Percent Mortality Illumination Time | |
| --- | --- | --- | --- |
| | | Fluorescent Light (18 hrs.) | Sunlight (20 min.) |
| Control | | 0.0 | 0.0 |
| Fluorescein Sodium | 61 | 0.0 | 0.0 |
| Rose Bengal | 102 | 53.3 | 47.5 |
| Rose Bengal: Fluorescein Sodium | 102:61 | 86.7 | 79.0 |

These data show that approximately 50 percent mortality of the larvae treated with Rose Bengal alone occurred 18 hours after exposure to fluorescent light, and occurred 20 minutes after exposure to sunlight. They also indicate that no mortality of larvae resulted when treated with fluorescein sodium alone. However, when fluorescein sodium was combined with Rose Bengal larval mortality produced by the mixture increased 62.7 percent under fluorescent light and increased 66.3 percent under sunlight when compared with the respective mortalities produced by the treatments with Rose Bengal alone. These data show the substantially enhanced (synergistic) insecticidal effect obtained on larvae of *A. triseriatus* by treatment with a combination of 0.6 part of the clearly non-insecticidal fluorescein sodium per part of the clearly insecticidal Rose Bengal.

EXAMPLE 2

A total of twenty 250 ml capacity transparent plastic dishes were each charged with 100 ml of distilled water and twenty fourth instar larvae of *Culex pipiens quinquefasciatus* were placed in each dish. A quantity of a $2.5 \times 10^{-3}$ M aqueous stock solution of Rose Bengal (w/v) sufficient to provide 4.0 ppm in final dilution was added to each dish in one set of five dishes and a quantity of a $2.5 \times 10^{-3}$ M aqueous stock solution of fluorescein sodium (w/v) sufficient to provide 4.0 ppm in final dilution was added to each dish in a second set of five dishes. Like quantities of each of the stock solutions were then added to each dish in a third set of five dishes to provide 4.0 ppm of Rose Bengal and 4.0 ppm of fluorescein sodium in combination in final dilution in each dish. The fourth set of five dishes was held as a control with only distilled water as the larval medium. One alfalfa tablet was added to each dish in all the sets of food, directly after which the larvae in the dishes were uniformly exposed to light for 24 hours from paired General Electric cool white fluorescent lamps. The photometer-measured intensity of the light at the surface of the solutions was 1200 $\mu E/m^2.sec$. Larval mortality was monitored at thirty minute intervals.

The above-described procedure was repeated in which seven additional concentrations of Rose Bengal and fluorescein sodium wherein 8, 16, 32, 64, 128, 256 and 512 ppm were used separately and in combination in equal parts. The percentages of mortality observed at various time intervals in these tests are summarized in Table II below.

TABLE II

Percent mortality of fourth instar *Culex pipiens quinquefasciatus* larvae upon treatment with the dye set fluorescein sodium/Rose Bengal and exposure to fluorescent light

| Treatment | Dose (ppm) | Percent Mortality Illumination time (hrs.) | | | | |
|---|---|---|---|---|---|---|
| | | 2 | 4 | 8 | 16 | 24 |
| Control | — | 0 | 0 | 0 | 0 | 0 |
| Fluorescein | 4 | 0 | 0 | 0 | 0 | 0 |
| | 8 | 0 | 0 | 0 | 0 | 0 |
| | 16 | 0 | 0 | 0 | 0 | 0 |
| | 32 | 0 | 0 | 0 | 0 | 0 |
| | 64 | 0 | 0 | 0 | 0 | 0 |
| | 128 | 0 | 0 | 0 | 0 | 0 |
| | 256 | 0 | 0 | 0 | 0 | 0 |
| | 512 | 0 | 0 | 0 | 0 | |
| Rose Bengal | 4 | 0 | 0 | 0 | 0 | 0 |
| | 8 | 0 | 0 | 0 | 0 | 0 |
| | 16 | 0 | 0 | 0 | 2.5 | 27.5 |
| | 32 | 0 | 0 | 2.6 | 28.2 | 53.8 |
| | 64 | 0 | 0 | 12.5 | 42.5 | 72.5 |
| | 128 | 0 | 0 | 17.5 | 55.0 | 92.5 |
| | 256 | 0 | 5.0 | 17.5 | 87.5 | 97.5 |
| | 512 | 0 | 7.5 | 20.0 | 95.0 | 97.5 |
| Rose Bengal: Fluorescein | 4:4 | 0 | 0 | 0 | 0 | 0 |
| | 8:8 | 0 | 0 | 2.5 | 17.5 | 32.5 |
| | 16:16 | 0 | 0 | 5.0 | 27.5 | 55.0 |
| | 32:32 | 0 | 0 | 10.0 | 40.0 | 77.5 |
| | 64:64 | 0 | 2.5 | 17.5 | 52.5 | 87.5 |
| | 128:128 | 0 | 5.0 | 27.5 | 90.0 | 100.0 |
| | 256:256 | 0 | 7.5 | 30.0 | 95.0 | 100.0 |
| | 512:512 | 0 | 7.5 | 35.0 | 100.0 | 100.0 |

These data show the synergistic insecticidal effect produced by fluorescein sodium in treating the larvae of *C. p. quinquefasciatus* with combinations in equal parts by weight of the clearly insecticidal Rose Bengal with the clearly noninsecticidal fluorescein sodium when compared with the percent mortality produced by an equal weight of Rose Bengal used singly. The synergistic effect is particularly pronounced between 8 and 16 hours and in dose levels from as low as 8 ppm of the insecticidal Rose Bengal ingredient of the mixture.

The comparative insecticidal activity of fluorescein sodium and Rose Bengal used individually and as combinations of equal weight concentrations to fourth instar *C. p. quinquefasciatus* in terms of $LT_{50}$ values (illumination time required for 50 percent mortality) as a function of dose concentration was determined by log transformation of values taken from Table II for probit analysis. The results are given in Table III below.

TABLE III

Time effectiveness on insecticidal activity of the dye set fluorescein sodium/Rose Bengal on *Culex pipiens quinquefasciatus* on exposure to fluorescent light

| Treatment | $LT_{50}$ (Hours of Illumination Dose Concentrations (ppm)) | | | | | | | |
|---|---|---|---|---|---|---|---|---|
| | 4 | 8 | 16 | 32 | 64 | 128 | 256 | 512 |
| Fluorescein Sodium | I | I | I | I | I | I | I | I |
| Rose Bengal | I | I | I | 22.3 | 16.9 | 13.1 | 9.9 | 9.0 |
| Rose Bengal: Fluorescein Sodium 1:1 | I | I | 22.5 | 16.6 | 13.4 | 9.2 | 8.3 | 6.8 |

I = No activity or data insignificantly regressed for analysis.

These data show the synergistic effect of fluorescein sodium on Rose Bengal in that combinations of equal parts by weight of non-insecticidal fluorescein sodium with insecticidal Rose Bengal produce approximately the same percent of mortality in fourth instar larvae of *C. p. quinquefasciatus* in approximately 20 to 25 percent less time that Rose Bengal used alone at the same concentration.

The insecticidal activity of fluorescein sodium and Rose Bengal used individually and as combinations of equal weight concentrations to fourth instar *C. p. quinquefasciatus* in terms of $LC_{50}$ values (the concentration required for 50 percent mortality within a specified time) was determined by log transformation of values taken from Table II for probit analysis. The results are presented in Table IV below.

TABLE IV

Concentration effectiveness on insecticidal activity of the dye set fluorescein sodium/Rose Bengal on *Culex pipiens quinquefasciatus* on exposure to fluorescent light

| Treatment | $LC_{50}$ (ppm) Hours of Illumination | | | | |
|---|---|---|---|---|---|
| | 2 | 4 | 8 | 16 | 24 |
| Fluorescein Sodium | I | I | I | I | I |
| Rose Bengal | I | I | I | 86.3 | 29.9 |
| Rose Bengal: Fluorescein Sodium 1:1 (Wt.) | I | I | I | 35.1 | 13.6 |

I = No activity or data insignificantly regressed for analysis.

These data indicated that approximately 55 to 60 percent lower concentrations of combinations of Rose Bengal and fluorescein sodium in equal parts by weight are required to effect approximately the same degree of insecticidal activity on *C. p. quinquefasciatus* exposed to fluorescent light as compared to concentrations of Rose Bengal used singly thus demonstrating the synergistic effect of fluorescein sodium on Rose Bengal.

EXAMPLE 3

Following the procedure described below, adult house flies (*Musca domestica*) from a laboratory reared strain were bioassayed for insecticidal effects of mixtures of erythrosine B with fluorescein sodium as compared to the insecticidal effects of erythrosine B per se. Eight to ten one-day-old adult house flies were counted into a clear plastic dish (250 ml capacity, 11.5 cm in diameter; and 4.5 cm deep) equipped with an aluminum screen cover and a 13 mm piece of cotton dental wicking inserted into a plastic cup resting on the bottom of the dish. Using a stock solution of $2.5 \times 10^{-3}$ M of the dye to be tested, a solution of known concentration of the dye in an aqueous 2 percent sucrose solution was prepared and applied, in excess, to the cotton wicking. The flies were held in total darkness for 24 hours prior to illumination during which time they fed only on the dye solution. Replications of eight to ten containers containing a total of 80 to 100 insects were prepared for eacy dye treatment. Control treatments without dye were similarly prepared.

After the 24 hour pretreatment in total darkness, the flies in the screen-covered dishes were uniformly exposed to light from paired General Electric cool white fluorescent lamps which provided a photometer-measured intensity of 1200 $\mu E/m^2.sec$ at a point midway in the depth of the container. No significant amount of heat was produced in the dish. Mortality was determined for the pretreatment (darkness) period and then at half-hourly intervals after initiation of illumination. Any insects which died prior to the light exposure were subtracted from the total number of insects pretreated.

The above-described exposure procedure was applied to the untreated control insects and to insects fed three concentrations of fluorescein sodium, five concentrations of erythrosine B and five mixtures of erythrosine B/fluorescein sodium comprised of approximately 0.43 parts by weight of fluorescein sodium for each part by weight of erythrosine B. The percentages of mortality observed at various time intervals in these tests are summarized in Table V below.

0.4 part by weight of fluorescein sodium for each part by weight of erythrosine B in treating adult house flies when compared with the percent mortality produced by an equal weight of erythrosine B used singly. The synergistic effect is particularly pronounced between 1.5 and 3.5 hours, and in dose levels from as low as 26.4 ppm of erythrosine B in combination with 11.2 ppm of fluorescein sodium.

The comparative insecticidal effectiveness of fluorescein sodium and erythrosine B at various concentrations used individually and in combinations of approximately 0.4 part by weight of fluorescein sodium for each part by weight of erythrosine B to adult house flies in terms of $LT_{50}$ values as a function of dose concentration was determined by log transformations of values given in Table V for probit analysis. The results are presented in Table VI below.

TABLE VI

Time effectiveness on insecticidal activity of the dye set fluorescein sodium/erythrosine B on *Musca domestica* on exposure to fluorescent light

| Treatment | $LT_{50}$ in hours of Illumination at (Dose concentrations in ppm) | | | | |
|---|---|---|---|---|---|
| Fluorescein Sodium | I (11.2) | I (22.7) | I (49.0) | I (94.5) | I (189.0) |
| Erythrosine B | I (26.4) | 14.1 (52.8) | 12.3 (114.4) | 4.2 (220.0) | 1.7 (440.0) |
| Erythrosine B: Fluorescein Sodium | 20.2 (26.4:11.2) | 10.9 (52.8:22.7) | 8.6 (114.4:49.0) | 3.2 (220.0:94.5) | 1.1 (440.0:189.0) |

I = No activity or data insignificantly regressed for analysis.

These data demonstrate the synergistic effect of fluorescein sodium when combined with erythrosine B in that combinations comprising approximately 0.4 part by weight of the non-insecticidal fluorescein sodium for each part by weight of the insecticidal erythrosine B produce approximately the same degree of mortality in adult house flies in approximately 22 to 35 percent less time than erythrosine B used alone at the same concentration.

The insecticidal activity of fluorescein sodium and erythrosine B used individually and as combinations in weight concentrations in the approximate ratio of 0.4 part by weight of fluorescein sodium per part by weight of erythrosine B, to adult house flies in terms of $LC_{50}$

TABLE V

Percent mortality of adult *Musca domestica* upon treatment with the dye set fluorescein sodium/erythrosine B and exposure to fluorescent light

| Treatment | Dose (ppm) | Percent Mortality Illumination Time (hours) | | | | | | | | | | |
|---|---|---|---|---|---|---|---|---|---|---|---|---|
| | | 0.3 | 0.5 | 7.0 | 1.5 | 2.0 | 2.5 | 3.0 | 3.5 | 4.0 | 12.0 | 24.0 |
| Control | — | 0 | 0 | 0 | 0 | 0 | 0 | 0 | 0 | 0 | 0 | 0 |
| Fluorescein Sodium | 11.2 | 0 | 0 | 0 | 0 | 0 | 0 | 0 | 0 | 0 | 0 | 0 |
| | 49.0 | 0 | 0 | 0 | 0 | 0 | 0 | 0 | 0 | 0 | 0 | 0 |
| | 189.0 | 0 | 0 | 0 | 0 | 0 | 0 | 0 | 0 | 0 | 0 | 0 |
| Erythrosine B | 26.4 | 0 | 0 | 0 | 0 | 0 | 0 | 0 | 0 | 0 | 14.1 | 33.3 |
| | 52.8 | 0 | 0 | 0 | 0 | 0 | 0 | 0 | 1.0 | 1.0 | 37.4 | 84.8 |
| | 114.4 | 0 | 0 | 1.0 | 3.0 | 4.0 | 7.0 | 11.0 | 16.0 | 21.0 | 47.0 | 98.0 |
| | 220.0 | 2.0 | 5.1 | 12.1 | 20.2 | 27.3 | 32.3 | 37.5 | 44.4 | 55.6 | 77.8 | 100.0 |
| | 440.0 | 6.1 | 15.2 | 29.3 | 42.7 | 60.6 | 65.7 | 66.7 | 73.7 | 78.8 | 89.9 | 100.0 |
| Erythrosine B: Fluorescein Sodium | 26.4:11.2 | 0 | 0 | 0 | 1.0 | 1.0 | 1.0 | 1.0 | 1.0 | 1.0 | 33.3 | 55.6 |
| | 52.8:22.7 | 0 | 0 | 1.0 | 2.0 | 3.0 | 3.0 | 4.0 | 5.0 | 5.0 | 54.5 | 90.9 |
| | 114.4:49.0 | 1.0 | 3.0 | 6.0 | 9.0 | 10.0 | 12.0 | 18.0 | 19.0 | 20.0 | 63.0 | 100.0 |
| | 220.0:94.5 | 5.1 | 16.2 | 22.2 | 28.3 | 34.3 | 40.4 | 45.5 | 52.5 | 60.6 | 80.8 | 100.0 |
| | 440.0:189.0 | 16.0 | 34.0 | 46.0 | 57.0 | 67.0 | 71.0 | 73.0 | 75.0 | 78.0 | 89.0 | 100.0 |

These data show that synergistic insecticidal effect at various concentrations produced by the non-insecticidal fluorescein sodium when combined with the insecticidal erythrosine B in a weight ratio of approximately values was determined by log transformation of values taken from Table V for probit analysis. The results are presented in Table VII below.

TABLE VII

Concentration effectiveness on insecticidal activity of the dye set
fluorescein sodium/erythrosine B on *Musca domestica* on exposure to fluorescent light

| Treatment | $LC_{50}$ (ppm) Hours of Illumination | | | | | | | | | | |
|---|---|---|---|---|---|---|---|---|---|---|---|
| | 0.3 | 0.5 | 1.0 | 1.5 | 2.0 | 2.5 | 3.0 | 3.5 | 4.0 | 12.0 | 24.0 |
| Fluorescein Sodium | I | I | I | I | I | I | I | I | I | I | I |
| Erythrosine B | I | I | 607.1 | 483.9 | 351.9 | 325.5 | 299.1 | 255.1 | 211.1 | 96.7 | 32.5 |
| Erythrosine B: | 1223: | 607.1: | 466.3: | 395.9 | 316.7: | 281.5: | 255.1: | 228.7: | 211.1: | 52.7: | 26.4: |
| Fluorescein Sodium (ppm) | 525.8 | 261.0 | 200.4 | 170.2 | 136.1 | 121.0 | 109.7 | 98.3 | 90.7 | 22.6 | 11.2 |

I = No activity or data insignificant regressed for analysis.

These data demonstrate the synergistic effect of fluorescein sodium on the insecticidal erythrosine B in that approximately the same degree of mortality of house flies can be achieved by utilizing combinations of erythrosine B with fluorescein sodium in the approximate ratio of 0.4 part by weight of fluorescein sodium per part by weight of erythrosine B as can be accomplished only by using larger amounts of erythrosine B singly. Thus, from approximately 10 to 20 percent less erythrosine B is required for equivalent $LC_{50}$ values in the mixtures with light exposure up to four hours and from approximately 25 to 40 percent less is required for light exposure from 12 to 24 hours.

EXAMPLE 4

Following the testing procedure described in Example 3 hereinabove, adult *Musca domestica* from a laboratory reared strain were bioassayed for insecticidal effects of mixtures of Rose Bengal with fluorescein sodium as compared to the insecticidal effects of Rose Bengal per se.

The procedure was applied to three concentrations of fluorescein sodium, five concentrations of Rose Bengal and five mixtures of Rose Bengal/fluorescein sodium comprised of approximately 0.37 parts by weight of fluorescein sodium for each part by weight of Rose Bengal. The percentages of mortality observed at various time intervals in these tests are summarized in Table VIII below.

TABLE VIII

Percent Mortality of adult *Musca domestica* upon treatment with the dye set fluorescein sodium/Rose Bengal and exposure to light

| Treatment | Dose (ppm) | Percent Mortality Illumination Time (hours) | | | | | |
|---|---|---|---|---|---|---|---|
| | | 0.5 | 1.0 | 1.5 | 2.0 | 2.5 | 3.0 |
| Control | — | 0 | 0 | 0 | 0 | 0 | 0 |
| Fluorescein Sodium | 11.2 | 0 | 0 | 0 | 0 | 0 | 0 |
| | 49.0 | 0 | 0 | 0 | 0 | 0 | 0 |
| | 189.0 | 0 | 0 | 0 | 0 | 0 | 0 |
| Rose Bengal | 30.6 | 0 | 0 | 0 | 0 | 0 | 0 |
| | 61.2 | 0 | 0 | 0 | 0 | 10 | 10 |
| | 132.6 | 0 | 4 | 20 | 32 | 48 | 56 |
| | 255.0 | 8 | 32 | 62 | 70 | 78 | 94 |
| | 510.0 | 6 | 14 | 34 | 58 | 80 | 84 |
| Rose Bengal: Fluorescein Sodium | 30.6:11.2 | 0 | 0 | 0 | 0 | 0 | 0 |
| | 61.2:22.7 | 0 | 0 | 0 | 0 | 6 | 22 |
| | 132.6:49.0 | 4 | 8 | 16 | 42 | 64 | 86 |
| | 255.0:94.5 | 14 | 32 | 60 | 82 | 98 | 100 |
| | 510.0:189.0 | 16 | 40 | 66 | 80 | 94 | 100 |

These data show the synergistic effect at the indicated concentrations produced by the non-insecticidal fluorescein sodium when combined with the insecticidal Rose Bengal in a ratio of approximately 0.37 part by weight of fluorescein sodium for each part by weight of Rose Bengal in treating adult house flies when compared with the percent mortality produced by an equal weight of Rose Bengal used singly. The synergistic effect is particularly pronounced between 2.0 and 3.0 hours, and in concentrations from as low as 49.0 ppm of fluorescein sodium in combination with 132.6 ppm of Rose Bengal.

The comparative insecticidal effectiveness against adult house flies of fluorescein sodium and Rose Bengal at various concentrations used individually and in admixture with each other in the ratio of approximately 0.37 part by weight of fluorescein sodium for each part by weight of Rose Bengal in terms of $LT_{50}$ values as a function of concentration was determined by log transformations of values given in Table VIII for probit analysis. The results are given in Table IX below.

TABLE IX

Time effectiveness on insecticidal activity of the dye set fluorescein sodium/Rose Bengal on *Musca domestica* on exposure to fluorescent light

| Treatment | $LT_{50}$ in Hours of Illumination at (Dose Concentrations ppm) | | | | |
|---|---|---|---|---|---|
| Fluorescein Sodium | I (11.2) | I (22.7) | I (49.0) | I (94.5) | I (189.0) |
| Rose Bengal | I (30.6) | I (61.2) | 2.6 (132.6) | 1.3 (255.0) | 1.7 (510.0) |
| Rose Bengal: Fluorescein Sodium | I $\begin{pmatrix} 30.6: \\ 11.2 \end{pmatrix}$ | I $\begin{pmatrix} 61.2: \\ 22.7 \end{pmatrix}$ | 1.8 $\begin{pmatrix} 132.6: \\ 49.0 \end{pmatrix}$ | 1.3 $\begin{pmatrix} 255.0 \\ 94.5 \end{pmatrix}$ | 1.1 $\begin{pmatrix} 510.0 \\ 189.0 \end{pmatrix}$ |

I = No activity or data significantly regressed for analysis.

The data of Table IX demonstrates that combinations comprising approximately 0.37 part by weight of the non-insecticidal fluorescein sodium for each part by weight of the insecticidal Rose Bengal produce approximately the same degree of mortality in adult house flies in approximately 30 to 35 percent less time than Rose Bengal used singly at the same concentration.

The insecticidal activity of fluorescein sodium and Rose Bengal used individually and as combinations in weight concentrations in the approximate ratio of 0.37 part by weight of fluorescein sodium per part by weight of Rose Bengal, to adult house flies in terms of $LC_{50}$ values was determined by log transformation of values taken from Table VIII for probit analysis. The results are presented in Table X below.

TABLE X

Concentration effectiveness on insecticidal activity of the dye set fluorescein sodium/Rose Bengal on *Musca domestica* on exposure to fluorescent light

| Treatment | $LC_{50}$ (ppm) Hours of Illumination | | | | | |
|---|---|---|---|---|---|---|
| | 0.5 | 1.0 | 1.5 | 2.0 | 2.5 | 3.0 |
| Fluorescein Sodium | I | I | I | I | I | I |
| Rose Bengal | I | I | 214.1 | 173.3 | 142.8 | 122.4 |
| Rose Bengal: Fluorescein Sodium | I | 540.4: 200.5 | 224.3: 83.2 | 142.8: 53.0 | 112.2: 41.6 | 91.7: 34.1 |

I = No activity or data insignificantly regressed for analysis

These data show the synergistic effect of fluorescein sodium on Rose Bengal in that approximately the same degree of mortality is effected on house flies by utilizing combinations of Rose Bengal and fluorescein sodium in the approximate ratio of 0.37 part by weight of fluorescein sodium per part by weight of Rose Bengal as can be effected only by using larger concentrations of Rose Bengal singly. Thus, approximately 18 percent less Rose Bengal is required in the mixture for equivalent $LC_{50}$ values with exposure to light for two hours and approximately 33 percent less is required for light exposure of 2.5 to 3.0 hours.

EXAMPLE 5

The testing procedure described in Example 2 hereinabove for bioassaying fourth instar larvae of *Culex pipiens quinquefasciatus* for the insecticidal effects of mixtures of Rose Bengal and fluorescein sodium as compared to the insecticidal effects of Rose Bengal used singly was followed for comparatively bioassaying second instar larvae of *Culex pipiens quinquefasciatus* with a mixture consisting of erythrosine B, Rose Bengal and fluorescein sodium in diffuse (shaded) solar light instead of in fluorescent light. The insecticidal effects of the three component mixture was compared with those of each of the components used singly with a mixture of Rose Bengal and erythrosine B. The test was conducted on a clear day in which the ambient temperature ranged from 9° to 13° C. and the photometer-measured intensity of the light at the surface of the solutions ranged from 460 to 700 $\mu E/m^2.sec$. The test results are given in Table XI below.

TABLE XI

Percent Mortality of second instar *Culex pipiens quinquefasciatus* larvae upon treatment with the dye set fluorescein sodium/erythrosine B/ Rose Bengal and exposure to diffuse solar light

| Treatment | Dose (ppm) | Percent Mortality Illumination Time (hrs.) | | | | |
|---|---|---|---|---|---|---|
| | | 1 | 2 | 3 | 4 | 5 |
| Control | — | 0 | 2 | 2 | 4 | 4 |
| Fluorescein Sodium | 10 | 0 | 2 | 2 | 2 | 2 |
| Rose Bengal | 10 | 0 | 14 | 24 | 26 | 32 |
| Erythrosine B | 10 | 0 | 6 | 18 | 22 | 26 |
| Rose Bengal: Erythrosine B | 10:10 | 0 | 14 | 24 | 24 | 36 |
| Rose Bengal: Erythrosine B: Fluorescein Sodium | 10:10:10 | 0 | 26 | 32 | 36 | 48 |

These data show the synergistic effect of fluorescein sodium on mixtures of erythrosine B and Rose Bengal in that a combination of Rose Bengal and erythrosine B used in equal parts by weight at a concentration of 10 ppm for pretreating the larvae in the dark followed by exposure to diffuse solar light for five hours, has essentially no greater insecticidal activity than Rose Bengal used singly in the same manner and that under the same conditions, the Rose Bengal-erythrosine B mixture additionally containing an equal part of fluorescein sodium at a concentration of 10 ppm, increases the insecticidal effectiveness by approximately one-third on exposure to light for five hours as compared with the insecticidal effectiveness of the Rose Bengal erythrosine mixture containing no fluorescein sodium.

EXAMPLE 6

Following the testing procedure described in Example 2 hereinabove for determining the insecticidal effects of treating fourth instar larvae of *Culex pipiens quinquefasciatus* with mixtures of Rose Bengal and fluorescein sodium as compared to the insecticidal effects of Rose Bengal used singly was followed for comparatively evaluating the insecticidal effects of a mixture consisting of equal parts by weight at a concentration of 10 ppm of erythrosine B, Rose Bengal and fluorescein sodium on first instar larvae of *Culex pipiens quinquefasciatus* as compared to the insecticidal effect of each of the components used singly and with a mixture of Rose Bengal and erythrosine B. The test was conducted at 24° C. and the photometer-measured intensity of the fluorescent light at the surface of the solutions was 1200 $\mu E/m^2.sec$. The test results are set forth in Table XII below.

TABLE XII

Percent Mortality of first instar *Culex pipiens quinquefasciatus* larvae upon treatment with the dye set fluorescein sodium/erythrosine B/Rose Bengal and exposure to fluorescent light

| Treatment | Dose (ppm) | Percent Mortality Illumination Time (hrs.) | | | | |
|---|---|---|---|---|---|---|
| | | 0.5 | 1.0 | 2.0 | 4.0 | 8.0 |
| Control | — | 0 | 2 | 2 | 4 | 4 |
| Fluorescein Sodium | 10 | 0 | 0 | 0 | 0 | 0 |
| Erythrosine B | 10 | 0 | 0 | 0 | 5.0 | 7.5 |
| Rose Bengal | 10 | 0 | 0 | 2.5 | 22.6 | 60.0 |
| Rose Bengal: Erythrosine B | 10:10 | 0 | 0 | 7.5 | 32.5 | 67.5 |
| Rose Bengal: Erythrosine B: Fluorescein Sodium | 10:10:10 | 0 | 0 | 5.0 | 45.0 | 77.5 |

These data show a 38 percent increase in the percent mortality after four hours and 5 percent increase after eight hours of exposure to fluorescent light effected by the 1:1:1 mixture at 10 ppm each of Rose Bengal, erythrosine B and fluorescein sodium over the 1:1 mixture of Rose Bengal and erythrosine B at 10 ppm each thus demonstrating the synergistic effect of fluorescein sodium on the insecticidal effectiveness of mixtures of erythrosine B and Rose Bengal.

EXAMPLE 7

Following the bioassay method described in Example 3 hereinabove, the effect of the ratio of fluorescein sodium to Rose Bengal was determined on adult house flies (*Musca domestica*). Two mixtures, one containing approximately 0.43 part by weight of fluorescein sodium for each part by weight of Rose Bengal, and the other consisting of approximately 4.3 parts by weight of fluorescein sodium for each part by weight of Rose Bengal were comparatively evaluated with reference to the insecticidal effectiveness of Rose Bengal used singly. The intensity of the fluorescent light at a point midway in the depth of the container was 1200 $\mu E/m^2$·sec and the ambient temperature was 24° C. The test data are set forth in Table XIII which follows.

TABLE XIII

Effect of the ratio of fluorescein sodium to Rose Bengal in the treatment of adult *Musca domestica* with the dye set fluorescein sodium/erythrosine B/Rose Bengal and exposure to fluorescent light

| Treatment | Dose (ppm) | Percent Mortality Illumination Time (hrs.) | | | | | |
|---|---|---|---|---|---|---|---|
| | | 0.5 | 1.0 | 1.5 | 2.0 | 2.5 | 3.0 |
| Control | — | 0 | 0 | 0 | 0 | 0 | 0 |
| Fluorescein Sodium | 189.0 | 0 | 0 | 0 | 0 | 0 | 0 |
| Rose Bengal | 440.0 | 0 | 31.3 | 45.9 | 45.7 | 62.0 | 75.0 |
| Rose Bengal: Fluorescein Sodium | 440.0:189.0 | 0 | 45.2 | 54.0 | 63.3 | 72.7 | 83.3 |
| Rose Bengal: Fluorescein Sodium | 440.0:1890.0 | 0 | 30.0 | 34.0 | 38.0 | 44.7 | 46.7 |

These data show that the above mixture containing 0.43 part by weight of fluorescein sodium for each part by weight of Rose Bengal has a higher percent mortality ranging from 44 percent at 1.0 hour to 11 percent at 3.0 hours than does Rose Bengal used singly in the same concentration while the mixture containing 4.3 parts (ten times) by weight of fluorescein sodium for each part by weight of Rose Bengal has a lowered percent mortality ranging from 4.2 percent at 1.0 hour to 38 percent at 3.0 hours. This demonstrates the synergistic insecticidal effect of fluorescein sodium produced on Rose Bengal when the parts by weight of the non-insecticidal fluorescein sodium in the mixture are less than the parts by weight of the insecticidal Rose Bengal, and the loss of said synergistic insecticidal effect when the parts by weight of fluorescein sodium are much greater than the parts by weight of Rose Bengal.

What is claimed is:

1. A synergistic insecticidal composition effective against insects of the family Muscidae and of the family Culicidae which is a mixture consisting essentially of an insecticidally effective amount of at least one insecticide chosen from the group consisting of erythrosine and Rose Bengal in combination with a synergistically effective amount of an alkali metal salt of fluorescein in the range of approximately 0.3 to 1.0 part by weight of the latter per part by weight of said insecticide.

2. A synergistic insecticidal composition according to claim 1 wherein the insecticide is erythrosine.

3. A synergistic insecticidal composition according to claim 1 wherein the insecticide is Rose Bengal.

4. A synergistic insecticidal composition according to claim 1 wherein the insecticide is a mixture of erythrosine and Rose Bengal.

5. A synergistic insecticidal composition according to claim 4 wherein the erythrosine, Rose Bengal and fluorescein sodium are in approximately equal parts by weight.

6. A synergistic insecticidal composition according to claim 1 containing an adjuvant selected from the group consisting of solid diluents, carriers and surface-active agents.

7. An aqueous solution containing an insecticidally effective amount of a synergistic insecticidal composition according to claim 1.

8. An aqueous solution of a synergistic insecticidal composition according to claim 1 containing an adjuvant selected from the group consisting of surface-active agents, dispersing agents and evaporation reducing agents.

9. A method for combating harmful insects of the family Muscidae and of the family Culicidae which comprises causing the insects to ingest an insecticidally effective amount of a composition according to claim 1 and exposing the insects to light.

* * * * *